United States Patent [19]

Feldman et al.

[11] Patent Number: 4,608,345

[45] Date of Patent: Aug. 26, 1986

[54] COLORIMETRIC DETECTION OF ALCOHOLS IN GASOLINE

[75] Inventors: Nicholas Feldman, Woodbridge; Jerome Panzer, Millburn, both of N.J.

[73] Assignee: Exxon Research and Engineering Co., Florham Park, N.J.

[21] Appl. No.: 668,575

[22] Filed: Nov. 5, 1984

[51] Int. Cl.$^4$ ............... G01N 31/00; G01N 33/03; G01N 33/26
[52] U.S. Cl. ............... 436/60; 252/408.1; 436/139
[58] Field of Search ............... 436/60, 139–143, 436/131, 132; 252/408.1

[56] References Cited

U.S. PATENT DOCUMENTS

| 2,968,940 | 1/1961 | Feldman et al. | 73/73 |
| 3,505,020 | 4/1970 | Caldwell | 23/230 |
| 4,070,154 | 1/1978 | Mascher et al. | 23/230 |

*Primary Examiner*—Frank Sever
*Attorney, Agent, or Firm*—Edward H. Mazer

[57] ABSTRACT

A colorimetric method for detecting the presence of alcohol in hydrocarbons, such as gasoline, is disclosed. The method comprises contacting the hydrocarbon with a mixture comprising:

i. an alcohol soluble, hydrocarbon insoluble dye; and
ii. a solid insoluble in hydrocarbon and alcohol whereby the mixture undergoes a color change in the presence of alcohol.

The hydrocarbon sample preferably is contacted with a drying agent to remove dissolved water prior to contacting the mixture.

14 Claims, No Drawings

COLORIMETRIC DETECTION OF ALCOHOLS IN GASOLINE

BACKGROUND OF THE INVENTION

This invention is directed at a method for detecting the presence of alcohols in hydrocarbon samples. More specifically, the present invention is directed at a colorimetric method for detecting the presence of alcohol in gasoline.

Frequently, it is necessary to determine if alcohol is present in hydrocarbons, such as gasoline. Alcohols, such as methanol, ethanol, and tertiary butanol, often are added to the gasoline pool to improve octane. However, the presence of alcohol, particularly in excess of about 1 volume percent, may cause several adverse effects. Since the alcohols are oxygenated compounds, their presence in gasoline may affect the oxygen to fuel ratio of the fuel being combusted leading to potential operational and emission problems. As a result, the United States Environmental Protection Administration currently limits the oxygen content of gasoline to less than 2 weight percent, (or up to 0.3 volume percent methanol) unless specific waivers have been granted.

In addition, the presence of excessive quantities of alcohol in gasoline may cause increased engine corrosion and adversely affect elastomeric engine seals.

In other instances, as for example in performing vapor pressure tests to determine the volatility of gasoline, the validity of test results may be dependent on the absence of alcohols. Tests which tolerate the presence of alcohols tend to be more elaborate and more expensive to perform. Hence, these alcohol-tolerant tests normally are conducted only when alcohols are known to be present in the sample tested.

Present methods for detecting the presence of alcohol in gasoline tend to be rather expensive, and usually require the use of elaborate analytical equipment operated by highly trained technicians. These methods are not readily adaptable for use by non-technically trained individuals in the field.

U.S. Pat. No. 4,070,154 discloses a method for measuring the alcohol content in jet fuel by mixing a known quantity of jet fuel with a known amount of an emulsion comprising a gel of finely grained particles saturated with a solution of sodium vanadiate, 8 hydroxyquinoline, water, acetic acid and an organic solvent which is free of OH-group chemicals and insoluble in water to form an emulsion matrix. The patent discloses that this mixture can be stored in a tube prior to use. A series of standards are prepared by preparing fuel samples with various known alcohol concentrations and passing these samples through tubes containing the mixture. The extent to which the emulsion matrix changes color in each standard tube is noted. The alcohol content of the fuel then is determined by adding a predetermined quantity of fuel to the mixture and noting the amount of the mixture that is discolored. This procecdure is not generally used because of the rather elaborate preparation required.

U.S. Pat. No. 2,968,940 discloses a method for detecting dispersed water in jet fuel and similar hydrocarbon oils, by contacting the fuel with a small amount of a mixture of finely divided, water-soluble, solid anhydrous dye and a finely-divided solid capable of taking up or adsorbing any water present in the sample. The dye required is the sodium salt of o-cresolsulfonphthalein and the finely divided solids were required to be anhydrous barium carbonate. Samples of the dye and finely divided solid are added to a sample of the fuel and agitated. The intensity of the color of the sample is compared with that of samples of known dispersed water content to determine the approximate dispersed water content of the sample. U.S. Pat. No. 3,505,020 discloses the use of a minor portion of fuchsia dye and a major proportion of a finely-divided, substantially anhydrous solid, i.e., calcium carbonate, barium carbonate, barium sulfate, magnesium carbonate and combinations thereof, to determine the approximate dispersed water content in jet fuels and similar hydrocarbon oils. A sample of the hydrocarbon is contacted with the dye-anhydrous solid mixture and agitated. The color change may be observed and compared to samples having known dispersed water contents to determine the approximate dispersed water content of the sample. The test procedures of these two U.S. patents may not be directly applicable to determining the alcohol content of gasoline, which often has a higher dissolved water content than the middle distillate fuels, such as jet fuel, since free water present would interfere with the test procedure for determining the alcohol content.

Accordingly, it would be desirable to provide a process which is a reliable, and inexpensive test for determining the presence of alcohol in hydrocarbon samples, such as gasoline.

It also would be desirable to provide a process which is easily used by non-technically trained individuals.

It also would be advantageous to provide a process which could be utilized in the field for qualitative screening of hydrocarbons, such as gasoline, for alcohol presence without the necessity of sending all samples for detailed analysis.

The present invention is directed at a method for determining the presence of alcohols, such as methanol, ethanol, the propanols and the butanols, in a hydrocarbon, such as gasoline, and comprises contacting the hydrocarbon with a mixture comprising:

A. an alcohol soluble, hydrocarbon insoluble dye; and,

B. an alcohol insoluble, hydrocarbon insoluble solid, and noting whether the mixtrue changes color. A color change indicates the presence of alcohol.

SUMMARY OF THE INVENTION

The present invention is directed to a method for detecting the presence of alcohol in hydrocarbon which comprises contacting the hydrocarbon with a mixture comprising:

i. an alcohol soluble, hydrocarbon insoluble dye; and ii. an alcohol insoluble, hydrocarbon insoluble solid, whereby the mixture undergoes a color change in the presence of alcohol.

The hydrocarbon preferably is treated with a drying agent, such as magnesium sulfate, sodium sulfate, calcium chloride or mixtures thereof, to remove water present in the hydrocarbon prior to the hydrocarbon contacting the dye mixture.

The dye comprises between about 0.1 and about 5 weight percent of the mixture, preferably between about 0.5 and about 1 weight percent of the mixture.

Among the preferred dyes are the following: hexamethyl p-rosaniline chloride, bromophenol blue, bromocresol green.

The hydrocarbon and alcohol insoluble solid preferably is finely divided and preferably is selected from the group consisting of salts of Group IIA metals, i.e., calcium, magnesium, barium, strontium. A preferred solid is calcium carbonate.

The alcohol detected typically will be methanol, ethanol, propanol, i.e., n-propanol and i-propanol, and/or butanol, i.e., n-butanol, sec. butyl alcohol, isobutanol and tertiary butyl alcohol, while the hydrocarbon frequently will be gasoline, although the test also may be applicable to middle distillate fuels, such as diesel fuel.

The concentration of the mixture in the hydrocarbon typically may range between about 0.1 grams and about 10 grams per 100 ml. of fuel, preferably between about 0.5 grams and about 1 gram per 100 ml of fuel.

DETAILED DESCRIPTION OF THE INVENTION

The present invention is directed at a colorimetric method for detecting the presence of the lower alcohols, such as methanol, ethanol, propanol and butanol in hydrocarbon samples, such as gasoline.

The present invention is not dependent upon the use of a particular dye. This invention may be practiced using any dye which is alcohol soluble and hydrocarbon insoluble. As used herein, the term "alcohol soluble dye" is defined to mean that the dye is sufficiently soluble to produce a color change in the presence of the alcohol. The term "hydrocarbon insoluble dye" is defined to mean that the dye does not produce a detectable color change in the presence of the hydrocarbon alone. Among the dyes which are alcohol soluble and hydrocarbon insoluble are the following: hexamethyl p-rosaniline chloride, bromphenol blue, bromcresol green, methylene blue, brilliant green, and orange one.

While the addition of alcohol soluble hydrocarbon insoluble dye directly to the hydrocarbon sample often may prove satisfactory, this method is not preferred because, while the quantity of dye required normally is very small, the dye may be relatively expensive. The addition of very small quantities of the dyes may lead to variations in the results obtained. In addition, the presence of color containing compounds in the sample tested may lead to erroneous test results.

To overcome these problems, the present invention is directed at pre-mixing the dye with a solid, preferably a relatively inexpensive finely divided solid which is insoluble in both the alcohol and the hydrocarbon. The alcohol insoluble solid preferably is of a color different from that of the dye when alcohol is present.

The present invention eliminates the problems of adding only small quantities of dye to the sample, since a relatively large quantity of the mixture is added. In addition, detection of a color change is facilitated if the alcohol and hydrocarbon insoluble solid is of a different color than the dye in the presence of an alcohol.

Preferred finely divided alcohol and hydrocarbon insoluble solids include the salts of Group IIA metals of the Periodic Table, i.e., calcium, magnesium, barium and strontium, such as calcium carbonate, calcium sulfate, calcium chloride, barium carbonate, barium sulfate, magnesium carbonate and mixtures thereof, with calcium carbonate being particularly preferred, since it is finely divided, insoluble in the test system, relatively inexpensive, non-toxic and presents a good background for detecting any color change in the system, since it is white.

The accuracy of the present invention is not affected adversely by the presence of gasoline dyes, corrosion inhibitors, detergents and antioxidants, or by other additives commonly present in gasoline.

The dye may comprise between about 0.01 and about 5 weight percent of the mixture, preferably between about 0.5 and about 1 weight percent. The concentration of the mixture in the hydrocarbon may range between about 0.1 and 10 grams per 100 ml. of fuel, preferably between about 0.5 and 1.0 grams per 100 ml. of fuel. The concentration of the dye in the mixture and the amount of the mixture added to the fuel will be dependent, in part, on the particular dye utilized.

Since dyes which are alcohol soluble normally also are at least partially soluble in water, it may be preferred to remove water present in the hydrocarbon sample. Failure to remove minor amounts of water present from the sample may result in the dye dissolving in the water even when alcohols are not present, thereby erroneously indicating the presence of alcohol. Minor amounts of water can be removed from the sample by the addition of a drying agent or desiccant, such as magnesium sulfate, sodium sulfate, calcium chloride or mixtures thereof. Addition of about 1 to about 10 grams of desiccant per 100 ml. of fuel sample, followed by brief shaking normally will remove water from the fuel sample subsequently drawn off.

The detectable limit of an alcohol depends on the particular dye used in the test. The presence of alcohol at concentrations above the detectable limit in the test sample will be evidenced by a color change of the alcohol insoluble solid within a relatively short period of time, i.e., about four minutes after the addition of the mixture to the fuel sample. If fuel samples containing the mixture are left for extended periods of time before the samples are checked for a color change, the erroneous presence of alcohols may be indicated by the dye dissolving in very small amounts of residual water present in the fuel.

For ease of handling and in order to facilitate the carrying out of the method of the invention, it will generally be found convenient to package the mixed dye and alcohol insoluble solid in capsules or ampules of polyethylene or a similar material. Each capsule may contain sufficient mixed dye and alcohol insoluble solid for one test. For relatively short periods of time it is sufficient to store the capsules in a tightly closed glass jar. Where the capsules are to be stored for extended periods of time or under severe weather conditions, it may be preferred to maintain them in a sealed vessel in the presence of a desiccant.

The exact nature and objects of the invention are further illustrated by the following examples.

As shown in the following Examples and tables, the present invention has been able to repeatedly detect alcohol concentrations as low as 0.05 volume percent methanol; 0.2 volume percent ethanol; and 0.3 volume percent tertiary butanol.

EXAMPLE 1

A mixture of 0.3 weight percent hexamethyl p-rosaniline chloride was admixed with about 99.7 weight percent calcium carbonate. Two hundred milligrams of this mixture was admixed with about 20 cc of gasoline containing varying amounts of methanol, ethanol and tertiary butanol. The presence of alcohol was determined by observing whether the calcium carbonate changed in color from white to pink. From the summary of test results shown as Table I, it can be seen that this method was able to detect methanol concentrations as low as 0.5 volume percent methanol and 1 volume percent ethanol.

TABLE 1

Detection of Alcohols Using Mixture Comprising 0.3 Weight Percent Hexamethyl P-Rosaniline Chloride and 99.7 Weight Percent Calcium Carbonate

| Alcohol Present | Alcohol Concentration Volume % | Color Change of Calcium Carbonate Detected |
|---|---|---|
| methanol | 0.5 | pink |
| 1:1 methalol:tert. butanol } | 0.5 | no change |
| 1:1 methanol:tert. butanol } | 1.0 | pink |
| ethanol | 0.5 | no change |
| ethanol | 1.0 | pink |

EXAMPLE 2

A mixture of 0.7 weight percent bromophenol blue and 99.3 weight percent calcium carbonate was prepared. To avoid any interference by dissolved water present in the gasoline, 1 gram of a drying agent, magnesium sulfate, was added to 20 ml. of gasoline and the sample was capped. The gasoline and drying agent were shaken for about 10 seconds and allowed to settle for at least two minutes. The supernatent gasoline layer was evacuated into a sealed tube containing about 200 milligrams of the dye-calcium carbonate mixture under vacuum. The gasoline, dye and calcium carbonate were intermixed by shaking for about 10 seconds and allowed to settle. The calcium carbonate changed from white to blue within less than four minutes if the alcohol contents of the gasoline were greater than the following: methanol 0.05 volume percent; ethanol 0.2 volume percent; tertiary butanol 0.3 volume percent.

A summary of the test data is set forth in Table II.

TABLE II

Detection of Alcohols Using Mixture Comprising 0.7 Weight Percent Bromophenol Blue and 99.3 Weight Percent Calcium Carbonate

| Alcohol Present | Alcohol Concentration Volume % | Color Change of Calcium Carbonate Detected |
|---|---|---|
| methanol | 0.05 | blue |
| 1:1 methanol:tert. butanol } | 0.1 | blue |
| ethanol | 0.1 | no change |
| ethanol | 0.2 | blue |
| tertiary butanol | 0.2 | no change |
| tertiary butanol | 0.3 | blue |

While the present method will not provide an accurate measurement of the alcohol content of the sample, the intensity and speed of the color change will be a function of the alcohol concentration and thereby a rough indicator of the quantity of alcohol present.

Although the present invention does not provide detailed analytical-type information on the sample tested, it does provide a simple, quick, and reliable screening method for determining the presence of alcohol. If necessary, more detailed analytical test procedures then could be conducted to determine the specific alcohol or alcohols present and their concentration in the sample.

What is claimed is:

1. A reliable, inexpensive method effectively usable even under field conditions by non-technically trained individuals comprising: detecting the presence of alcohol in hydrocarbon by contacting the hydrocarbon with a mixture including:
   i. an alcohol soluble, hydrocarbon insoluble dye; and
   ii. a solid insoluble in hydrocarbon and alcohol, and causing the mixture to undergo a color change in the presence of alcohol.

2. The method of claim 1 wherein the solid insoluble in hydrocarbon and alcohol comprises a salt of a Group IIA metal.

3. The method of claim 2 wherein the salt is selected from the group consisting of calcium carbonate, calcium sulfate, barium carbonate, calcium chloride, magnesium carbonate and mixtures thereof.

4. The method of claim 2 wherein the hydrocarbon is contacted with a drying agent prior to contacting the mixture.

5. The method of claim 4 wherein the dye comprises between about 0.01 and about 5 weight percent of the mixture.

6. The method of claim 5 wherein the dye comprises between about 0.5 and about 1 weight percent of the mixture.

7. The method of claim 5 wherein the concentration of the mixture in the hydrocarbon ranges between about 0.1 and about 10 grams per 100 ml. of the hydrocarbon.

8. The method of claim 7 wherein the concentration of the mixture in the hydrocarbon ranges between about 0.5 and about 1.0 grams per 100 ml. of hydrocarbon.

9. The method of claim 7 wherein the hydrocarbon is gasoline.

10. The method of claim 9 wherein the alcohol is selected from the group consisting of methanol, ethanol, propanol, butanol and mixtures thereof.

11. The method of claim 10 wherein the dye is selected from the group of dyes consisting of hexamethyl p-rosaniline chloride, bromophenol blue, bromocresol green, methylene blue, brilliant green, orange one and mixtures thereof.

12. A method comprising detecting the presence of alcohol in gasoline having minor amounts of water by,
   A. contacting the gasoline with a drying agent adapted to remove minor amounts of water; and
   B. contacting the gasoline with a mixture comprising:
      i. an alcohol soluble, hydrocarbon insoluble dye; and
      ii. a solid insoluble in gasoline and alcohol; and causing the mixture to undergo a color change in the presence of alcohol thereby providing a reliable, inexpensive method effectively usable even under field conditions by non-technically trained individuals.

13. The method of claim 12 wherein the drying agent is selected from the group consisting of magnesium sulfate, sodium sulfate, calcium chloride and mixtures thereof.

14. A method comprising: detecting the presence of methanol, ethanol, propanol, butanol, or mixtures thereof in a gasoline sample having dissolved water therein by,
   A. contacting the gasoline with a drying agent adapted to remove dissolved water;
   B. subsequently contacting the gasoline with a mixture comprising:
      i. an alcohol soluble, hydrocarbon insoluble dye; and
      ii. a solid insoluble in gasoline and alcohol; and causing the mixture to undergo a color change in the presence of alcohol to thereby provide a relatively reliable inexpensive method effectively usable even under field conditions by non-technically trained individuals.

* * * * *